United States Patent
Harada

(10) Patent No.: US 10,307,285 B2
(45) Date of Patent: Jun. 4, 2019

(54) DEFORMED NAIL CORRECTOR

(71) Applicant: Masanori Harada, Kitakyushu (JP)

(72) Inventor: Masanori Harada, Kitakyushu (JP)

( * ) Notice: Subject to any disclaimer, the term of this patent is extended or adjusted under 35 U.S.C. 154(b) by 138 days.

(21) Appl. No.: 15/039,032

(22) PCT Filed: Nov. 27, 2014

(86) PCT No.: PCT/JP2014/081376
§ 371 (c)(1),
(2) Date: May 25, 2016

(87) PCT Pub. No.: WO2015/080200
PCT Pub. Date: Jun. 4, 2015

(65) Prior Publication Data
US 2017/0020709 A1    Jan. 26, 2017

(30) Foreign Application Priority Data

Nov. 29, 2013 (JP) .................. 2013-248727
Dec. 27, 2013 (JP) .................. 2013-270878

(51) Int. Cl.
*A61F 5/11*    (2006.01)

(52) U.S. Cl.
CPC .................... *A61F 5/11* (2013.01)

(58) Field of Classification Search
CPC ...... A61F 5/05875; A61F 5/0118; A61F 5/10; A61F 2013/00093; A61F 5/05866;
(Continued)

(56) References Cited

U.S. PATENT DOCUMENTS 1,596,532 A * 8/1926 Haener .................. A61F 5/11
602/31
4,057,055 A   11/1977 Clark
(Continued)

FOREIGN PATENT DOCUMENTS

| EP | 2481382 A | 8/2012 |
| JP | H08-215227 A | 8/1996 |

(Continued)

OTHER PUBLICATIONS

International Search Report for PCT/JP2014/081376 dated Jan. 27, 2015.
(Continued)

*Primary Examiner* — Ophelia A Hawthorne
*Assistant Examiner* — Caitlin A Carreiro
(74) *Attorney, Agent, or Firm* — Yokoi & Co., U.S.A.; Toshiyuki Yokoi

(57) ABSTRACT

The corrector includes a band-shaped central region to be in contact with an upper surface of the nail; and an insertion edge region continuously extended from at least one end of the band-shaped central region to be inserted between a lateral nail edge and a lateral nail fold, wherein when a direction of a base side of the nail is defined as an upstream and a direction of a tip side of the nail is defined as a downstream in a state that the corrector is attached to the nail, a screw impeller-shaped portion having a specific shape and dimension is formed on a portion including an end portion of an upstream side of the insertion edge region and a hook portion is formed on a downstream side of the insertion edge region to hold the lateral nail edge of the nail or a lateral edge of a nail tip.

14 Claims, 5 Drawing Sheets

(58) Field of Classification Search
CPC ...... A61F 13/10; A61F 13/105; A61F 2/7812; A61F 5/11; A41D 13/082; A41D 19/01588
USPC .......... 602/12, 22, 63, 31, 30; 128/880; 2/21
See application file for complete search history.

(56) References Cited

U.S. PATENT DOCUMENTS

| | | | |
|---|---|---|---|
| 6,050,966 A | | 4/2000 | Wilberscheid |
| 6,095,995 A | | 8/2000 | Machida |
| 6,231,840 B1 | * | 5/2001 | Buck ........................ A61K 8/36 424/405 |
| 2009/0211197 A1 | * | 8/2009 | Stolz ........................ A61F 5/11 52/749.1 |
| 2010/0137771 A1 | | 6/2010 | Harada |
| 2010/0160845 A1 | | 6/2010 | Yoshikawa |
| 2010/0228173 A1 | * | 9/2010 | Ishida ........................ A61F 5/11 602/31 |

FOREIGN PATENT DOCUMENTS

| | | |
|---|---|---|
| JP | 2001-276104 A | 10/2001 |
| JP | 2002-360619 A | 12/2002 |
| JP | 2004-238288 A | 8/2004 |
| JP | 2007-229509 | 9/2007 |
| JP | 2007-244851 A | 9/2007 |
| JP | 2011-024776 A | 2/2011 |
| JP | 2011-104231 A | 6/2011 |
| JP | 4964233 A | 4/2012 |
| WO | 2008/142880 A | 11/2008 |

OTHER PUBLICATIONS

PCT written openion dated Jan. 27, 2015.
Japanese decision to grant a patent dated Jul. 7, 2014.
Kazuya Matsumoto, et al., Resin splint as a new conservative treatment for ingrown toenails, The journal of Medical Investigation vol. 57, Aug. 2010, 321 to 325 pages.
The extended European search report dated Sep. 6, 2017.

* cited by examiner

Fig. 11A
Fig. 11B
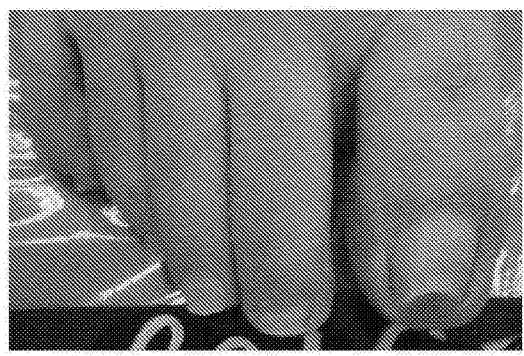 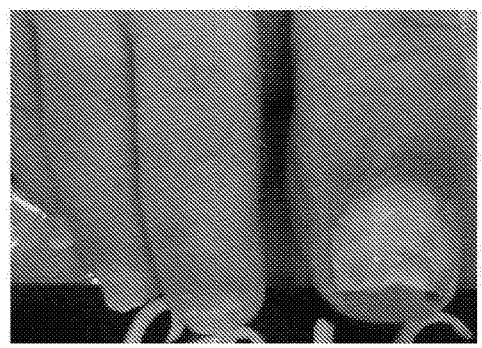

DEFORMED NAIL CORRECTOR

TECHNICAL FIELD

The present invention relates to a deformed nail corrector. In more detail, the present invention relates to a deformed nail corrector formed in a band shape and configured to be attached to a nail along a direction crossing a longitudinal direction of the nail, comprising: a band-shaped central region configured to be in contact with an upper surface of the nail; and an insertion edge region continuously extended from at least one end of the band-shaped central region and configured to be inserted between a lateral nail edge and a lateral nail fold, wherein when a direction of a base side of the nail is defined as an upstream and a direction of a tip side of the nail is defined as a downstream in a state that the corrector is attached to the nail, a screw impeller-shaped portion having a specific shape and dimension is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip. The present invention also relates to a kit for correcting a deformed nail including a pair of deformed nail correctors attached to both left and right sides of a nail and a system for correcting a deformed nail formed by combining the pair of deformed nail correctors. When the corrector of the present invention is used, the screw impeller-shaped portion and the hook portion are cooperated with each other, and therefore the corrector can be inserted into a lateral portion of a root of the nail without giving pain even for a serious ingrown nail which is significantly deformed and curved. In order to efficiently correct the nail, the lateral portion of the root of the nail is the most important portion. Thus, a great effect of the correction can be obtained while a patient burden is reduced.

BACKGROUND ART

Nail deformity includes "rolled nail" and "ingrown nail." Frequently, the word of the rolled nail and the word of the ingrown nail are used without being distinguished from each other. However, in general, a state as if the nail is rolled laterally is called as "rolled nail," and a state that the nail is significantly curved and both ends of the nail are growing into skin or flesh (soft tissue) is called as "ingrown nail" in many cases. In case of the ingrown nail, one or both sides of lateral edges of the nail are deeply growing into a nail groove along with the growth of the nail, and stuck in the soft tissue (flesh inside the nail) causing inflammation accompanying pain or severe pain. The ingrown nail is mainly caused by pressure, wound, overcut and birth defect, for example. The ingrown nail frequently occurs especially on a big toe. As the conventionally known method for curing the ingrown nail, a method of removing the lateral edge of the nail ingrown in the nail groove by a surgical operation, a method of using a corrector or a correcting device, and a method of using a treatment agent for the correction are known, for example. As the method of using the corrector and the correcting device, for example, U.S. Pat. No. 4,057,055 (Patent Document 1), Japanese Unexamined Patent Application Publication No. H08-215227 (Patent Document 2), Japanese Unexamined Patent Application Publication No. 2001-276104 (Patent Document 3), Japanese Unexamined Patent Application Publication No. 2011-104231 (Patent Document 4) and Japanese Unexamined Patent Application Publication No. 2002-360619 (Patent Document 5) can be seen. As the method of using the treatment agent for the correction, Japanese Unexamined Patent Application Publication No. 2004-238288 (Patent Document 6) can be seen. Furthermore, as a device preferably used for the process of using the treatment agent for the correction, the device described in WO2008-142880 (Patent Document 7) is known.

However, the method of using the surgical operation is complicated and the width of the nail plate becomes narrow permanently after the operation. Furthermore, in the method of using the surgical operation, the nail growing into the soft tissue is partly cut and removed. Thus, the operation is difficult when there is a risk of bacterial infection. Even if the ingrown nail is temporarily cured by the surgical operation by partly removing the nail, tendency of curling in a curling direction is not corrected as whole the nail. Thus, the ingrown nail often occurs again after the operation. Consequently, it is now generally thought that a method not using the surgical operation, i.e. a conservative method, is preferable as the method for curing the ingrown nail.

The method of using the corrector or the correcting devise will be described below. For example, Patent Document 1 proposes a devise that includes post members adhered to both lateral edges of an outer surface of a nail having the ingrown part along the longitudinal direction of a finger having the nail, and a tension member such as a rubber string, wherein the post members have a vertical part to hold the tension member, and the post members adhered to the both lateral edges of the outer surface of the nail are pulled toward each other by the tension member to lift up the both lateral edges of the nail. In Patent Document 2, a method of curing the rolled nail is proposed by adhering a plate-like piece made of shape memory alloy or shape memory resin on a curved surface of the rolled nail using an adhesive agent and then raising the environmental temperature to a predetermined temperature or more to use a restoring force of the plate-like piece. In Patent Document 3, a corrector for correcting deformation of the nail and a correcting method using the corrector are proposed as explained below. The corrector for correcting deformation of the nail described in Patent Document 3 is formed to hook a hook portion of a wire or the like on the ingrown part of both lateral edges of the nail so as to pull the both lateral edges of the ingrown nail toward the center direction. More specifically, the corrector includes a first engagement portion to be engaged with one lateral edge in the width direction of a nail body, a first correcting body having a first contact portion to be in contact with a part of the surface of the nail body and a first connecting hook portion to be connected with the first contact portion, a second engagement portion to be engaged with the other lateral edge in the width direction of the nail body, a second correcting body having a second contact portion to be in contact with a part of the surface of the nail body and a second connecting hook portion to be connected with the second contact portion, and a correcting operation portion that is engaged with the first connecting hook portion and the second connecting hook portion to hold the first connecting hook portion and the second connecting hook portion in a state of being pulled toward the center portion side in the width direction of the nail body by a predetermined hanging force so that the one lateral edge and the other lateral edge of the nail body are hanged up. Patent Document 4 discloses an orthosis for the rolled nail formed by a triangle-shaped plate having a U-shaped groove on one side of the triangle and a metal hooking fitting on an apex opposed to the groove, and a hook formed in S-shape so that an axis of the hook is rotated 90° between both ends.

In the device described in Patent Document 1, however, a force applied to the both lateral edges of the ingrown nail is larger in the direction of pulling the nail toward the center direction than the upper direction which is required for extracting the ingrown part from the nail groove. Thus, it is difficult to obtain an appropriate effect of the correction. In addition, several months are required for a treatment when using this devise. However, the post member of the device described in Patent Document 1 has a vertical part, and therefore it is very difficult to live a daily life while the device is attached. Consequently, the device described in Patent Document 1 is not practical. Furthermore, in the nail deformity such as the ingrown nail, the nail is deeply growing into the skin/flesh of the nail groove even at a place near the root. In addition, the nail is covered by a posterior nail fold and cannot be seen. Consequently, the nail is growing into the nail groove at the root of the nail and the curvature of the lateral portion of the nail covered by the posterior nail fold should be corrected in order to obtain a sufficient effect of the correction and prevent the ingrown nail from occurring again. Since this devise basically acts only on the center part of the exposed nail, significant correcting effect cannot be expected. In particular, as a problem, this devise is not suitable for correcting the serious ingrown nail where the lateral edges of the nail is deeply growing into the skin/flesh and the ingrown nail occurs again as the nail grows long.

In the method described in Patent Document 2, since the plate-like piece made of shape memory alloy or shape memory resin is adhered on the nail surface by the adhesive agent, the nail surface cannot follow the plate-like piece when the plate-like piece is flattened. As a result, when adhesive strength of the adhesive agent is low, the plate-like piece is easily peeled off from the nail surface. On the contrary, when the adhesive strength is too high, restoring force of the plate-like piece is obstructed or other inconveniences may occur. Furthermore, the above described plate-like piece acts only on the center part of the exposed nail. Thus, there is the same problem as Patent Document 1.

In the method described in Patent Document 3, same as the case of using the above described plate-like piece, several months are required for a treatment. Also, since the patient should live a daily life while the corrector is attached, this method is very painful for the patient. In addition, in this method, since the hook of the wire is hooked on the lateral edges of the ingrown nail, pain and bleeding are often accompanied. For the patient, the problem is not only in pain. As another problem, this method cannot be applied to the patient when the nail is hard or brittle and cannot be applied to the patient of tinea unguium. Furthermore, since the ingrown part is lifted up by the hook having a thin wire-shaped hook, the force is necessarily applied to only a part of the lateral edges of the nail. Thus, it is difficult to evenly and efficiently correct the curvature of the lateral edges of the nail. In addition, as explained above, in the nail deformity such as the ingrown nail, the root part deeply growing into the skin/flesh of the nail groove cannot be seen in many cases. Thus, it is very difficult to hook the hook of the wire on the above described part without imparting burdens to the patient. Consequently, as a problem, the curvature of the root part of the nail cannot be solved eventually and the deformation of the nail occurs again.

The triangle-shaped orthosis disclosed in Patent Document 4 aims for efficient correction in a state that the nail edge is engaged with the wide U-shaped groove formed on one side of the triangle. However, the U-shaped groove is too long and has a constant cross-sectional shape over the entire length. In case of the serious ingrown nail or when the edge part of the nail is deformed into a nonlinear shape, in particular, the orthosis is difficult to be attached. Thus, practicality is low. In addition, because of the shape of the orthosis, it is difficult to attach the orthosis on the root of the nail without imparting burdens to the patient. Thus, there is the same problem as the above described Patent Document 1 and the like.

Patent Document 5 discloses a corrector of ingrown nail having an operation portion to be held in a hand by an operator, a contact portion to be in contact with the nail, and a tip groove having an approximately J-shape in a cross-section provided on the contact portion so as to be inserted into the ingrown part of the nail, wherein the operator corrects the curved state of the ingrown nail by moving the corrector in a state that the tip groove is inserted into the ingrown part of the nail, the corrector and the nail are adhered with each other in the corrected state, the corrector is shaped to fit the shape of the nail so as to be integrated with the nail in appearance, and then an unnecessary part is removed as the nail grows long. Furthermore, in Non-Patent Document 1, an example of the treatment using a tool (splint) based on substantially same technical concept with Patent Document 5 is reported. In the corrector shown in the figures of Patent Document 5, it seems at a glance that the corrector is designed to be inserted to the root of the nail. However, in practice, as explained above, Patent Document 5 only discloses that only "tip groove" of the corrector is attached to the tip portion of the nail. For example, in the example shown in FIG. 1 of Patent Document 5, the width of the tip groove to be inserted into a reverse side of the nail is disclosed as 3 mm. Of course, the tip groove having the width of 3 mm cannot be assumed to be inserted into the root of the nail. In actual, as described above, Patent Document 5 only discloses that "tip groove" is inserted. In the figures, a state that only the tip portion is inserted is shown. Note that the above described width of 3 mm is considered to be the minimum width required for securing a size and strength when considering the technical concept of Patent Document 5, i.e., the nail is corrected by twisting the nail in a state that the end portion of the nail is held by the tip groove.

If the corrector has the above described shape as disclosed in Patent Document 5, heavy burdens are placed on the patient when the corrector is tried to be inserted to the root of the nail. In the embodiment shown by the picture in Non-Patent Document 1, actually, only an extremely short area of the tip is inserted between the lateral nail edge and the lateral nail fold, i.e., a portion that the nail is growing into the skin. As a result, the effect of the correction is applied only to the tip of the nail and surrounding area. Accordingly, an effect of the corrector of Patent Document 5 is weak for correcting the serious ingrown nail. In addition, the root of the nail is not sufficiently corrected and the ingrown nail occurs again as the nail grows. In addition, same as the case of Patent Document 4, the tip groove of the corrector of Patent Document 5 has a constant cross-sectional shape over the entire length. Accordingly, when the lateral edge of the nail is deformed in an irregular shape, for example, it is sometimes difficult to insert the corrector to the root of the nail by force.

The method of using treatment agent for the correction described in Patent Document 6 will be described below. Patent Document 6 discloses a treatment agent for a deformed nail such as an ingrown nail including one kind of a reducing agent selected from a group consisting of cysteine, thioglycolic acid and thioglycolic acid salt, and discloses a correcting method using the treatment agent. In the invention of Patent Document 6, focusing on the fact that the composition of the nail is similar to the composition of the hair, permanent waving technique for the hair is applied to the correction of the nail. More specifically, the following operations are performed. An emulsifier is added to the above described reducing agent, which is a main component of the first agent for the permanent waving, to obtain a cream-type medicine containing 5 wt. % of the reducing agent. Thus, the obtained agent is used as the treatment agent for the deformed nail. First, the nail (deformed nail such as an ingrown nail) is grown long enough and two or three small through holes are formed on the grown part (free edge) located at the tip of the nail. Then, the above described treatment agent is applied to the whole external surface of the nail and left to stand for approximately 30 minutes to reduce and cut disulfide bond of the cysteine contained in a keratin protein in the nail forming two mercapto groups. Thus, the nail is softened. The treatment agent is washed and removed by warm water. After the nail is softened as described above, the shape of the nail is corrected by the operator, an ordinary temperature-curable resin is applied to the external surface of the nail to fix the nail so that the small through holes formed at the free edge of the nail, left to stand for approximately 1 hour, and then the resin for fixing the nail is removed. However, the operator corrects the nail by fingers in this method. Accordingly, the operation is complicated and requires skilled hand. In addition, the nail should be grown long enough to fix the nail after the correction. However, many patients of the ingrown nail overcut the nail. Thus, as a problem, the correction operation cannot be performed immediately in many cases. Furthermore, the root of the nail is basically not corrected. Thus, there is the same problem as Patent Document 5 and the like.

Patent Document 7 discloses a devise for correcting the ingrown nail by lifting up a nail edge portion ingrown in the nail groove including: a vertical push-down member provided with a push-down head at a lower end of the push-down member; a lift-up angle maintaining means extended in a horizontal direction, the push-down member is attached to an intermediate part of the lift-up angle maintaining means; and a pair of lift-up members extended below from two positions of the lift-up angle maintaining means, the two positions are opposite to each other with respect to the intermediate part to which the push-down member attached, anchors are held on the lower end of the lift-up members, wherein a tension is applied to the lift-up members of the device attached to the external surface of the nail, the lift-up force to correct the ingrown nail is applied to the anchors attached to both lateral portions of the external surface of the nail, and the intermediate portion of the external part of the nail is pushed toward the thickness direction of the finger by the push-down head of the push-down member. In particular, if the above described correcting device is used together with the nail softener described in Patent Document 6, for example, the ingrown nail can be surely corrected without giving pain to the patient by a simple operation within a short time of approximately 30 minutes to 1 hour. However, there is a need to take necessary steps to maintain the shape of the nail after the correction treatment and prevent the ingrown nail from occurring again. Actually, there is no suitable means for achieving this purpose.

PRIOR ART DOCUMENTS

Patent Documents

Patent Document 1: U.S. Pat. No. 4,057,055
Patent Document 2: Japanese Unexamined Patent Application Publication No. H08-215227
Patent Document 3: Japanese Unexamined Patent Application Publication No. 2001-276104
Patent Document 4: Japanese Unexamined Patent Application Publication No. 2011-104231
Patent Document 5: Japanese Unexamined Patent Application Publication No. 2002-360619
Patent Document 6: Japanese Unexamined Patent Application Publication No. 2004-238288
Patent Document 7: International Patent Publication WO2008-142880

Non-Patent Documents

Non-Patent Document 1: J. Med. Invest. 2010 August; 57(3-4): 321-5. "Resin splint as a new conservative treatment for ingrown toenails," K. Matsumoto et. al.

SUMMARY OF THE INVENTION

Problems to be Solved by the Invention

As described above, in general, in the nail deformation such as the ingrown nail, the nail is deeply growing into the skin/flesh of the nail groove even at a place near the root. In addition, the nail is covered by a posterior nail fold and cannot be seen. Consequently, the nail is growing into the nail groove at the root of the nail and the curvature of the lateral portion of the nail covered by the posterior nail fold should be corrected in order to obtain a sufficient effect of the correction and prevent the ingrown nail from occurring again. In the conventional deformed nail corrector, only the tip or the center part of the nail can be corrected. Thus, as a problem, the curvature of the above described part is not be solved and the ingrown nail occurs again as the nail grows long. Even if the conventional corrector is tried to be attached to the root of the nail by force in order to solve the above described problem, the soft tissue of the nail groove is damaged. When the shape of the lateral edge of the nail is deformed into an irregular shape, the corrector is difficult to be attached to the root of the nail from the beginning. From the above, it is desired to provide such a corrector that can be easily inserted into near the root of the nail without giving pain to the patient enabling to obtain a great effect of the correction without causing the deformation again even when the deformation and the curvature of the nail to be corrected are serious or when the lateral edge of the nail is irregularly deformed.

Means for Solving Problem

In such a situation, as a result of intensive research to solve the above described problem, the inventor found that the problem can be solved by a deformed nail corrector formed in a band shape and configured to be attached to a nail along a direction crossing a longitudinal direction of the nail, comprising: a band-shaped central region configured to be in contact with an upper surface of the nail; and an insertion edge region continuously extended from at least one end of the band-shaped central region and configured to be inserted between a lateral nail edge and a lateral nail fold, wherein when a direction of a base side of the nail is defined as an upstream and a direction of a tip side of the nail is defined as a downstream in a state that the corrector is attached to the nail, a screw impeller-shaped portion having a specific shape and dimension is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip. In particular, the inventor found that the corrector could be smoothly inserted into the root of the nail without giving pain to the patient regardless of degree and condition of the deformation of the deformed nail to be corrected because of the above described specific structure of the insertion edge region. In accordance with this knowledge, the present invention is completed.

Effects of the Invention

If the corrector of the present invention is used, even when the deformation and the curvature of the nail to be corrected is serious or when the lateral edge of the nail is irregularly deformed, the corrector can be inserted into the root of the nail without giving pain to the patient. Thus, a great effect of the correction is obtained and the deformation of the nail is prevented from occurring again.

BRIEF DESCRIPTION OF THE DRAWINGS

FIGS. 11A and 11B are photographs of a toe of a patient of the second example before and after the correction treatment.

EMBODIMENTS OF THE INVENTION

Figure 1:
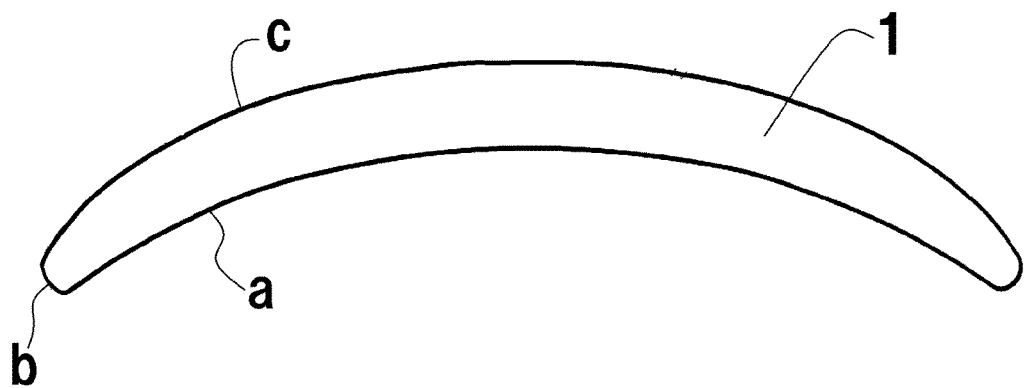
FIG. 1 is a front view of a nail.

The present invention provides a deformed nail corrector formed in a band shape and configured to be attached to a nail along a direction crossing a longitudinal direction of the nail, comprising:

a band-shaped central region configured to be in contact with an upper surface of the nail; and an insertion edge region continuously extended from at least one end of the band-shaped central region and configured to be inserted between a lateral nail edge and a lateral nail fold, wherein when a direction of a base side of the nail is defined as an upstream and a direction of a tip side of the nail is defined as a downstream in a state that the corrector is attached to the nail, a screw impeller-shaped portion is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip, the screw impeller-shaped portion has a shape curved downward at an angle of 90° or less, in a state that the deformed nail corrector is attached to the nail, a length of the screw impeller-shaped portion measured along the direction crossing the longitudinal direction of the nail is increased from the upstream side to the downstream side and is equal to or more than 5% of a width of the insertion edge region measured along the longitudinal direction of the nail, and the hook portion is curved downward at an angle of 90° or more.

Next, in order to assist the understanding of the present invention, a basic feature and various preferable embodiments of the present invention will be listed.

1. A deformed nail corrector formed in a band shape and configured to be attached to a nail along a direction crossing a longitudinal direction of the nail, comprising:

a band-shaped central region configured to be in contact with an upper surface of the nail; and an insertion edge region continuously extended from at least one end of the band-shaped central region and configured to be inserted between a lateral nail edge and a lateral nail fold, wherein when a direction of a base side of the nail is defined as an upstream and a direction of a tip side of the nail is defined as a downstream in a state that the corrector is attached to the nail, a screw impeller-shaped portion is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip, the screw impeller-shaped portion has a shape curved downward at an angle of 90° or less, in a state that the deformed nail corrector is attached to the nail, a length of the screw impeller-shaped portion measured along the direction crossing the longitudinal direction of the nail is increased from the upstream side to the downstream side and is equal to or more than 5% of a width of the insertion edge region measured along the longitudinal direction of the nail, and the hook portion is curved downward at an angle of 90° or more.

2. The deformed nail corrector according to claim 1, wherein when a maximum value of the length of the screw impeller-shaped portion is defined as 100%, a minimum value of the length of the screw impeller-shaped portion is 90% or less.

3. The deformed nail corrector according to claim 1, wherein when a maximum value of the length of the screw impeller-shaped portion is defined as 100%, a minimum value of the length of the screw impeller-shaped portion is 80% or less.

4. The deformed nail corrector according to any one of claim 1, wherein the screw impeller-shaped portion includes at least one area selected from a group consisting of a first area where the length of the screw impeller-shaped portion is linearly increased from the upstream side to the downstream side, a second area where the length of the screw impeller-shaped portion is stepwisely increased from the upstream side to the downstream side, a third area where the length of the screw impeller-shaped portion is increased from the upstream side to the downstream side in a curvature swelling outward, and a fourth area where the length of the screw impeller-shaped portion is increased from the upstream side to the downstream side in a curvature recessed inward.

5. The deformed nail corrector according to any one of claims 1 to 4, wherein at least the insertion edge region is formed of a flexible material.

6. The deformed nail corrector according to any one of claims 1 to 5, wherein a length of the band-shaped central region measured along the direction crossing the longitudinal direction of the nail is more than 50% of a width of the nail to which the deformed nail corrector is attached.

7. The deformed nail corrector according to any one of claims 1 to 6, further comprising:

an extension portion that is extended from at least one selected from a group consisting of the end portion of the upstream side of the deformed nail corrector and an end portion of the downstream side of the deformed nail corrector to support to fix the deformed nail corrector on the nail.

8. The deformed nail corrector according to any one of claims 1 to 7, wherein:

at least one handle is formed on an upper surface of the band-shaped central region.

9. The deformed nail corrector according to any one of claims 1 to 8, wherein:

two insertion edge regions are extended from both ends of the band-shaped central region, the band-shaped central region has a shape to function as a pull spring, the two insertion edge regions are inserted into both left and right sides of the nail, and a force is applied to the nail to fasten the nail from the left and right sides of the nail when the deformed nail corrector is attached to the nail.

10. The deformed nail corrector according to any one of claims 1 to 9, wherein:

the deformed nail corrector is used for the nail softened and shaped by a nail softener including a substance acting as a reducing agent of disulfide bond.

11. A kit for correcting a deformed nail including a pair of deformed nail correctors formed in a band shape and configured to be attached to both left and right sides of a nail, each of the deformed nail corrector comprising:

a band-shaped central region configured to be in contact with an upper surface of the nail; and an insertion edge region continuously extended from at least one end of the band-shaped central region and configured to be inserted between a lateral nail edge and a lateral nail fold, wherein when a direction of a base side of the nail is defined as an upstream and a direction of a tip side of the nail is defined as a downstream in a state that the corrector is attached to the nail, a screw impeller-shaped portion is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip, the screw impeller-shaped portion has a shape curved downward at an angle of 90° or less, in a state that the deformed nail corrector is attached to the nail, a length of the screw impeller-shaped portion measured along the direction crossing the longitudinal direction of the nail is increased from the upstream side to the downstream side and is equal to or more than 5% of a width of the insertion edge region measured along the longitudinal direction of the nail, and the hook portion is curved downward at an angle of 90° or more.

12. A system for correcting a deformed nail combining a pair of deformed nail correctors formed in a band shape and configured to be attached to both left and right sides of a nail, each of the deformed nail corrector comprising:

a band-shaped central region configured to be in contact with an upper surface of the nail; and an insertion edge region continuously extended from at least one end of the band-shaped central region and configured to be inserted between a lateral nail edge and a lateral nail fold, wherein when a direction of a base side of the nail is defined as an upstream and a direction of a tip side of the nail is defined as a downstream in a state that the corrector is attached to the nail, a screw impeller-shaped portion is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip, the screw impeller-shaped portion has a shape curved downward at an angle of 90° or less, in a state that the deformed nail corrector is attached to the nail, a length of the screw impeller-shaped portion measured along the direction crossing the longitudinal direction of the nail is increased from the upstream side to the downstream side and is equal to or more than 5% of a width of the insertion edge region measured along the longitudinal direction of the nail, the hook portion is curved downward at an angle of 90° or more, and the pair of the deformed nail correctors formed in the band shape are laminated at the band-shaped central region and fixed with each other by an adhesive agent.

Hereafter, with reference to the attached drawings, the present invention will be explained in detail.

FIG. 1 is a front view of a nail 1. In case of the above described corrector disclosed in Patent Document 5, for example, a tip groove (groove for housing a tip portion of the nail) of the corrector has an approximately J-shape in cross-section over the entire length. Namely, when the corrector of Patent Document 5 is pushed in from the tip to the root side of the nail, at the lateral edge of the nail, the tip groove should be pushed into a soft tissue of a lower surface "a" and a lateral surface "b". In some cases, the tip groove should be pushed into a soft tissue around an upper surface "c". Although the tip groove is rounded at a tip end portion facing the lower surface "a" of the nail, the tip groove have a constant shape over the entire length at a portion facing the lateral surface "b" and the upper surface "c" of the nail. If the corrector is inserted into the root of the nail, of course, heavy burdens are placed on the patient. Accordingly, in Patent Document 5, only the tip of the lateral portions of the ingrown nail is inserted into the tip groove, and the corrector is rotated in the width direction of the nail, i.e., the direction crossing the longitudinal direction of the nail, in a state that the tip is held by the tip groove so as to twist the tip of the nail and correct the nail. As a result, basically, only the tip of the nail and its surrounding area are corrected. However, the curvature of the ingrown nail is started from the root of the nail. Thus, the ingrown nail may occur again as the nail grows long.

Figure 2:
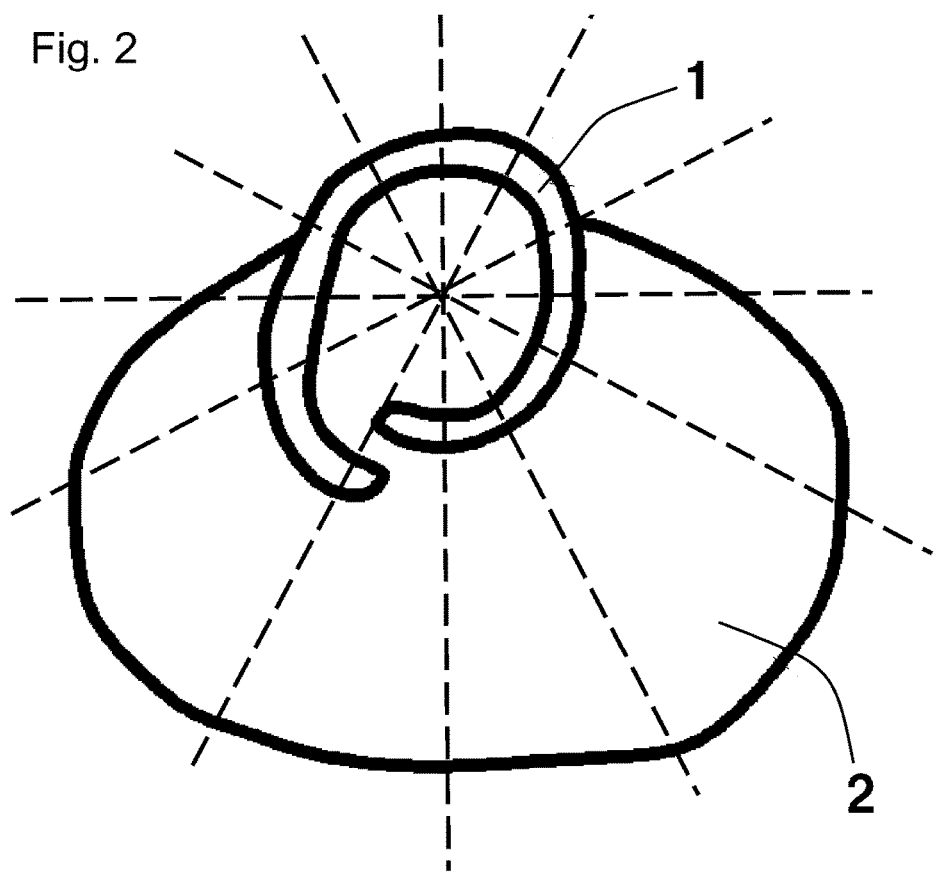
FIG. 2 is a front view of a big toe having an ingrown nail (broken lines show 12 directions shifted by an equal angle (30°) from the center of a circle of a curved nail which is curved in an approximately circular shape).

In particular, in case of the serious ingrown nail, the curvature may become 360° or more as shown in FIG. 2. In this example, in the right side of the finger when viewed from the front, the nail is growing into the skin/flesh from the direction of three o'clock to seven o'clock. When the ingrown nail is in such a state, even if the curvature of the nail is solved only at the tip portion of the nail and its surrounding area, enough and persistent correcting effect cannot be obtained. Accordingly, it is difficult to correct such a serious ingrown nail described above by the corrector disclosed in Patent Document 5. In addition, in the technology that the plate-like corrector is adhered to only the exposed surface of the nail as disclosed in Patent Document 2, it is difficult to provide the correcting effect to the curvature of the lateral portion of the nail growing into the nail groove. Furthermore, even if the nail edge is tried to be engaged with the wide U-shaped groove as shown as the orthosis described in Patent Document 4, the root of the nail is growing into the lateral surface "b" of the nail as shown in FIG. 1 and cannot be seen. Thus, it is difficult to engage the lateral surface "b" of the root of the nail with the above described U-shaped groove without imparting burdens to the patient. In the corrector shown in Patent Document 2 and Patent Document 5, a groove for housing a lateral edge of the nail has a constant cross-sectional shape over the almost entire length. Accordingly, when the lateral edge of the nail is irregularly deformed, it is difficult to insert the corrector into the root of the nail by force in some cases.

On the contrary, in the corrector of the present invention, when the corrector is inserted in the direction from the tip to the root of the nail, the screw impeller-shaped portion gradually holds the lateral surface "b" of the nail initially, and then the hook portion holds from the lateral surface "b" to the lower surface "a". In case of actual use, when the corrector is pushed from the tip of the nail, the screw impeller-shaped portion is smoothly entered between the lateral edge and the soft tissue as if the screw impeller-shaped portion slides into there, and then the hook portion is smoothly inserted into the root of the nail while being led by the screw impeller-shaped portion. Thus, the corrector can be attached without imparting burdens to the soft tissue into which the nail is growing. In the corrector of the present invention, the screw impeller-shaped portion is formed on a portion including the lateral end portion (portion that comes into contact with the nail first) of the upstream side of the insertion edge region of the corrector. The screw impeller-shaped portion has a shape curved downward at an angle of 90° or less. In a state that the corrector is attached to the nail, a length of the screw impeller-shaped portion measured along the direction crossing the longitudinal direction of the nail is increased from the upstream side to the downstream side and is equal to or more than 5% of a width of the insertion edge region measured along the longitudinal direction of the nail. In addition, the hook portion is formed on the downstream side of the insertion edge region in comparison to the screw impeller-shaped portion. The hook portion is curved downward at an angle of 90° or more.

Figure 3:
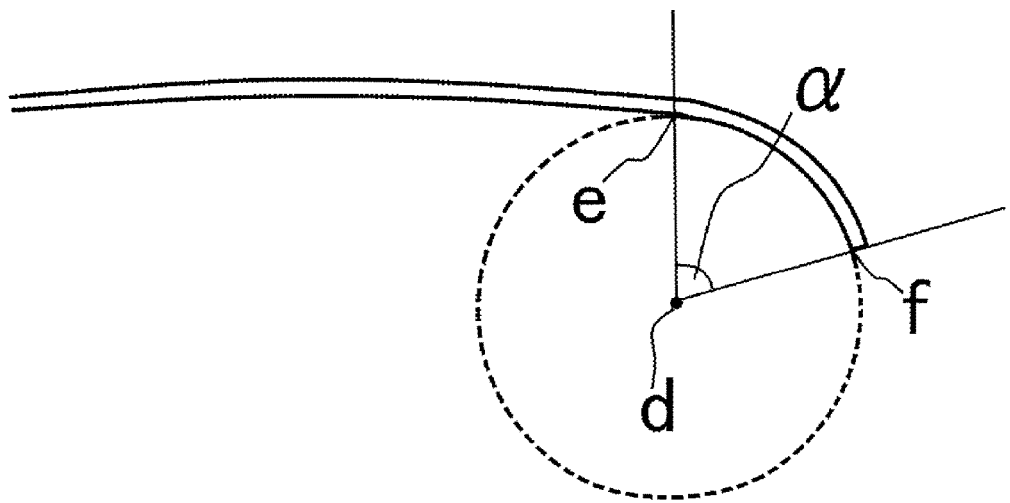
FIG. 3 is an explanatory drawing showing a curvature angle of an insertion edge region of a corrector of the present invention (broken lines show a circle drawn by extending the curvature of the insertion edge region of the corrector of the present invention).
Figure 8:
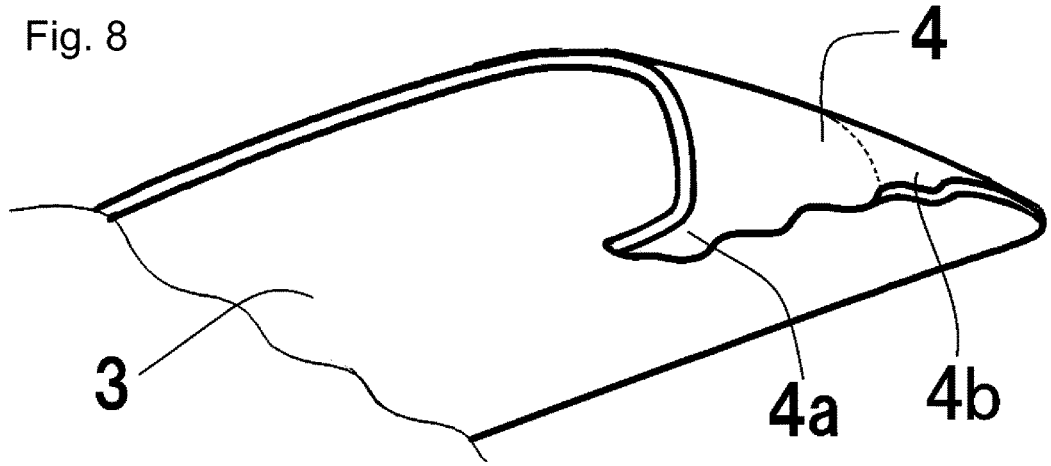
FIG. 8 is a schematic cross-sectional view of a corrector of another embodiment of the present invention seen obliquely from below.

Here, the angle of the curvature of the screw impeller-shaped portion and the hook portion is measured, as shown in FIG. 3 which shows the corrector of the present invention viewed from the front, by assuming a circle (shown by a broken line in FIG. 3) formed by extending a curved portion (line e-f in FIG. 3) or a similar circle, drawing a line d-e connecting a center "d" of the circle and a starting point of curvature "e" and a line d-f connecting the center "d" and a tip portion "f" of the screw impeller-shaped portion (or the hook portion), and measuring a center angle α (80° in an example of FIG. 3) formed between the line d-e and the line d-f. If the screw impeller-shaped portion (or the hook portion) is curved completely to the starting point, the angle α is 360°. If the curve is a semicircle the angle α is 180°. If the curve is a quarter of the circle, the angle α is 90°. Note that the hook portion can include a portion having less curvature forming an approximately U-shape as a whole as shown in FIG. 8. In such a case, the angle α of the curvature is decided by using the same method described above by assuming the circle formed by extending a curved portion started from a border between the band-shaped central region and the hook portion, i.e., ignoring the portion having less curvature. The above explanation is also applied when the screw impeller-shaped portion has a portion having less curvature forming an approximately L-shape as a whole.

In the corrector disclosed in Patent Document 5, it is important to hold the end portion of the nail by the tip groove so that the tip portion of the nail is not removed from the tip groove when the corrector is twisted. On the contrary, in the corrector of the present invention, as described above, since the screw impeller-shaped portion is formed, when the corrector is attached to the nail, the screw impeller-shaped portion slides on the lateral portion of the nail and inserted into the root of the nail without imparting burdens to the affected part. When the corrector of the present invention is used, even if a case of the serious ingrown nail shown in FIG. 2, for example, the corrector can be inserted into the root of the nail without difficulty. Consequently, the ingrown nail can be corrected efficiently. As can be seen from the above description, the technical concepts of the present invention and Patent Document 5 are completely opposite from each other.

The corrector of the present invention will be explained specifically with reference to FIGS. 4 to 9.

A deformed nail corrector of the present invention is a deformed nail corrector formed in a band shape and configured to be attached to a nail along a direction crossing a longitudinal direction of the nail, comprising: a band-shaped central region 3 configured to be in contact with an upper surface of the nail; and an insertion edge region 4 continuously extended from at least one end of the band-shaped central region 3 and configured to be inserted between a lateral nail edge (side line) and a lateral nail fold (side wall).

The band-shaped central region 3 is an area to be in contact with the upper surface of the nail. The dimension and shape of the area is not particularly limited. In order to secure operability or for other purposes, the length of the area can be specified to be much longer than the width of the nail before attached to the nail so that unnecessarily part is cut after attachment. In general, as the area of the band-shaped central region 3 adhered to the surface of the nail becomes large, the corrector can be more stably fixed on the surface of the nail. Thus, the length of the band-shaped central region 3 is preferred to be more than 50% of the width of the nail to which the corrector is attached. However, even when the area of the band-shaped central region 3 adhered to the surface of the nail is small, the corrector may be stably fixed on the surface of the nail or the surface of the finger in some cases, such as when the insertion edge region 4 is stably fixed on the nail or the finger. In such cases, the length of the band-shaped central region 3 can be less than 50% of the width of the nail to which the corrector is attached. Accordingly, the preferable length of the band-shaped central region 3 depends on the degree of necessity of strongly fixing the band-shaped central region 3 on the upper surface of the nail. When the degree of necessity of strongly fixing the band-shaped central region 3 on the upper surface of the nail is relatively high, specifically, the length of the band-shaped central region 3 measured along the direction crossing the longitudinal direction of the nail is normally 3-25 mm, preferably 5-20 mm and more preferably 7-15 mm. However, as described above, from the viewpoint of the operability of the attachment, the length of the area can be specified to be longer than the above described range so that unnecessarily part is cut after attached to the nail. On the contrary, when the degree of necessity of strongly fixing the band-shaped central region 3 on the upper surface of the nail is relatively low, specifically, the length of the band-shaped central region 3 measured along the direction crossing the longitudinal direction of the nail is normally 5 mm or less, preferably 5-0.1 mm, more preferably 4-0.1 mm, more preferably 3-0.1 mm, more preferably 2-0.1 mm, and more preferably 1-0.1 mm. However, as described above, from the viewpoint of the operability of the attachment, the length of the area can be specified to be longer than the above described range so that unnecessarily part is cut after attached to the nail. The width of the band-shaped central region 3 measured along the longitudinal direction of the nail can be arbitrarily selected according to the size of the applicable nail or other conditions. The width of the band-shaped central region 3 is normally 0.2 to 20 mm, preferably 2 to 20 mm, more preferably 3 to 15 mm, and more preferably 4 to 9 mm. The thickness of the band-shaped central region 3 is specified to be inconspicuous when the corrector of the present invention is attached. From the viewpoint of improving the feeling when attached to the nail, the thickness is preferably thin. However, in consideration of elasticity for securing strength and correcting force, the thickness can be selected from the range of normally 0.05 to 5 mm, preferably 0.1 to 5 mm, more preferably 0.2 to 2 mm, and more preferably 0.4 to 1.0 mm. The band-shaped central region 3 can be a flat plate-shape. Alternatively, the band-shaped central region 3 can be a curved shape to be fit with the shape of the surface of the nail. However, from the viewpoint of easiness of attaching the corrector and obtaining sufficient correcting effect, a curvature radius R of the band-shaped central region 3 should be larger than a curvature radius R of the hook portion. If the band-shaped central region 3 is a flat plate-shape, an effect like a plate spring can be obtained from the band-shaped central region 3. On the contrary, if the band-shaped central region 3 is curved, there is an advantage of easily attaching the corrector to the nail. The structure of the band-shaped central region 3 is not particularly limited. The structure of the band-shaped central region 3 can be even or uneven. For example, the band-shaped central region 3 can have one, two or more small holes. Both the length of the band-shaped central region 3 measured along the direction crossing the longitudinal direction of the nail and the width of the band-shaped central region 3 measured along the longitudinal direction of the nail can be even or uneven. The material of the band-shaped central region 3 can be same as the material of the insertion edge region 4 or can be different from the material of the insertion edge region 4. The property of the band-shaped central region 3 is not particularly limited. The property of the band-shaped central region 3 can be a hard material, a soft material, a flexible material, or an elastic material. The material of the band-shaped central region 3 is not particularly limited. The material of the band-shaped central region 3 can be a resin, a metal, an elastomer, a rubber, or a non-woven fabric, for example. The band-shaped central region 3 can be formed by a metal wire or a resin wire, for example. Alternately, the band-shaped central region 3 can be formed by a belt-like body or a string-like body made of an elastomer or a rubber. As long as the purpose of the present invention is achieved, an adhesive tape or an adhesive plaster can be used as the material of the band-shaped central region 3, for example.

In the corrector of the present invention, basically, a portion to be in contact with the upper surface of the nail is defined as the band-shaped central region 3, and a portion continuously extended from the band-shaped central region 3 and not in contact with the upper surface of the nail is defined as the insertion edge region 4. Even when the band-shaped central region 3 has a curved shape and a border between the band-shaped central region 3 and the insertion edge region 4, which includes the hook portion 4a and the screw impeller-shaped portion 4b, is not clear, the curvature radius R of the hook portion is smaller than the curvature radius R of the band-shaped central region 3 and therefore a point where the curvature radius R is changed can be recognized as the border between the band-shaped central region 3 and the hook portion 4a. In case the border between the screw impeller-shaped portion 4b and the band-shaped central region 3 is not clear at a glance, the border between the band-shaped central region 3 and the screw impeller-shaped portion 4b is considered to be located on an extended line of the border between the band-shaped central region 3 and the hook portion 4a. When a direction of a base side of the nail is defined as an upstream and a direction of a tip side of the nail is defined as a downstream in a state that the corrector is attached to the nail, the curvature radius R of the upstream side and the curvature radius R of the downstream side can be different from each other. For example, the curvature radius R can be gradually increased from the upstream side to the downstream side so that the insertion edge region 4 has an approximately conical shape.

In the present invention, when a direction of a base side of the nail is defined as an upstream and a direction of a tip side of the nail is defined as a downstream in a state that the corrector is attached to the nail, a screw impeller-shaped portion 4b is formed on a portion including an end portion of an upstream side of the insertion edge region 4 and a hook portion 4a is formed on a downstream side of the insertion edge region 4 in comparison to the screw impeller-shaped portion 4b to hold a lateral nail edge of the nail or a lateral edge of a nail tip, and the screw impeller-shaped portion 4b has a shape curved downward at an angle of 90° or less. In addition, in a state that the corrector is attached to the nail, a length of the screw impeller-shaped portion 4b measured along the direction crossing the longitudinal direction of the nail is increased from the upstream side to the downstream side and is equal to or more than 5% of a width of the insertion edge region measured along the longitudinal direction of the nail, and the hook portion 4a is curved downward at an angle of 90° or more. The screw impeller-shaped portion 4b is preferably 5 to 99% of the width of the insertion edge region 4, more preferably 7 to 80%, and particularly preferably 10 to 60%.

The angle α of the curvature of the screw impeller-shaped portion 4b is preferably 1 to 90°, more preferably 5 to 90°, and further more preferably 8 to 90°. The angle of the curvature of the screw impeller-shaped portion 4b of the upstream side can be different from that of downstream side. Furthermore, it is preferred that the angle of the curvature is designed to increase gradually from the upstream side to the downstream side. For example, the distance from the end portion of the upstream side to the downstream side of the screw impeller-shaped portion 4b is defined as 100%, the angle of the curvature is preferably 1 to 18° at an area within 20% from the end portion of the upstream side, preferably 18 to 36° at an area within 20% to 40% from the end portion of the upstream side, preferably 36 to 54° at an area within 40% to 60% from the end portion of the upstream side, preferably 54 to 72° at an area within 60% to 80% from the end portion of the upstream side, and preferably 72 to 90° at an area within 80% to 100% from the end portion of the upstream side. Since the most optimal angle of the curvature varies depending on the patient, the angle of the curvature can be arbitrarily adjusted in accordance with the individual case when actually performing the treatment.

When the maximum length of the screw impeller-shaped portion 4b (the distance measured along the width direction of the nail from the border between the screw impeller-shaped portion 4b and the band-shaped central region 3 to the tip of the screw impeller-shaped portion 4b) is defined as 100%, the minimum length of the screw impeller-shaped portion 4b is preferably 90% or less, more preferably 80% or less, more preferably 70% or less, more preferably 60% or less, more preferably 50% or less, more preferably 40% or less, more preferably 30% or less, more preferably 20% or less, more preferably 10% or less, and more preferably 5% or less. In addition, the length is preferably the minimum (e.g. 0%) at the end portion of the upstream side of the screw impeller-shaped portion 4b. An actual length of the longest part of the screw impeller-shaped portion 4b, i.e., a part having the maximum length, is normally 10 mm or less, preferably 6 mm or less, and more preferably 4 mm or less.

A specific shape of the screw impeller-shaped portion 4b is not particularly limited as long as the above described conditions are satisfied. For example, the screw impeller-shaped portion 4b can include at least one area selected from a group consisting of an area where the length is linearly increased from the upstream side to the downstream side (e.g., 4b shown in FIG. 5), an area where the length is stepwisely (gradually step by step) increased from the upstream side to the downstream side (e.g., 4b shown in FIG. 8), an area where the length is increased from the upstream side to the downstream side in a curvature swelling outward (e.g., 4b shown in FIG. 6), and an area where the length is increased from the upstream side to the downstream side in a curvature recessed inward (e.g., 4b shown in FIG. 6). In addition, as shown 4b in FIG. 8, an area where the length is not changed can be partly provided.

Figure 9:
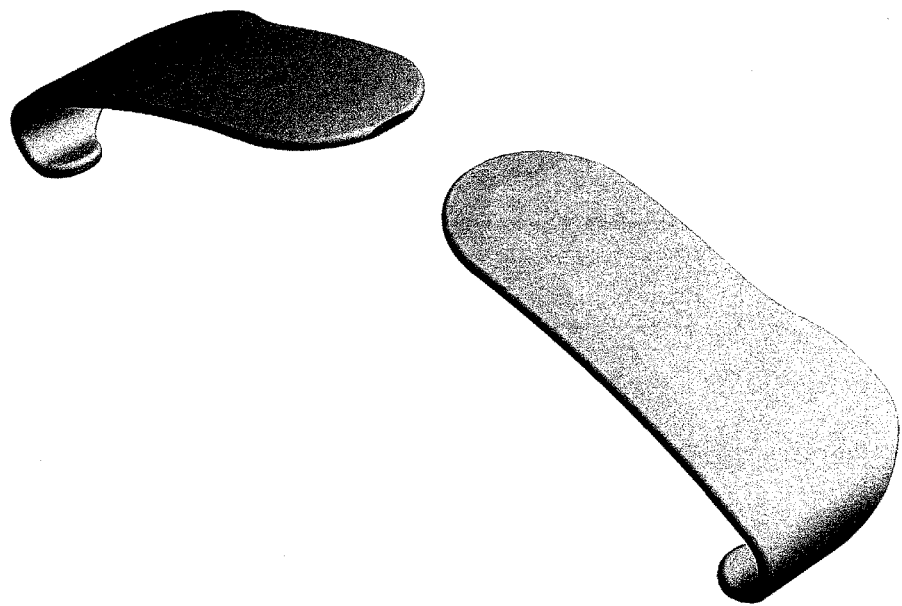
FIG. 9 is a schematic cross-sectional view of a pair of correctors of the present invention seen obliquely from above.

The width of the band-shaped central region 3 and the width of the insertion edge region 4, which are measured along the longitudinal direction of the nail, can be same or different from each other. For example, when the width of the band-shaped central region 3 is set to be wider than the width of the insertion edge region 4 so as to cover larger area of the surface of the nail, the correcting effect can be improved. On the contrary, as a case of setting the width of the insertion edge region 4 wider, as shown in FIG. 9, the width of the band-shaped central region 3 can be set to same width as the insertion edge region 4 only at a border between the band-shaped central region 3 and the insertion edge region 4 while a surrounding area of the border between the band-shaped central region 3 and the insertion edge region 4 is curved and protruded at the end portion of the upstream side. In the above described embodiment, the burdens imparted to the soft tissue of the ingrown nail can be further reduced when attaching the corrector. In particular, the above described embodiment is effective for the serious ingrown nail, such as when the upper surface ("c" in FIG. 1) is remarkably covered by the soft tissue.

The material of the corrector of the present invention is not particularly limited as long as the above described effects of the present invention can be obtained. Various materials such as various resins and metals, elastomers and rubbers can be used. The band-shaped central region 3 and the insertion edge region 4 can be made from different materials. As an example, the band-shaped central region 3 and the screw impeller-shaped portion 4b can be made of a resin, while the hook portion 4a can be made of a metal. As another example, the band-shaped central region 3 can be made of a metal wire, a resin wire, or a belt-like body or a string-like body made of an elastomer or a rubber. As long as the effects of the present invention can be obtained, the band-shaped central region 3 can be made by an adhesive tape or an adhesive plaster.

In the present invention, it is preferred that at least the insertion edge region 4, especially the screw impeller-shaped portion 4b, is formed of a flexible material. For the flexible material, a flexible resin can be used, for example. As an example of the available resin, polycarbonate, ABS resin (acrylonitrile-butadiene-styrene copolymer), nylon (polyamide), tenite acetate, vinyl acetate, polyvinyl chloride, polyethylene, polypropylene, polyethylene terephthalate, fluorocarbon resin, acrylic-based resin, urethane-based resin, polyether sulfone resin (PES) and polyphenyl sulfone resin (PPSU) can be listed. These resins can be used independently or used in combination. As a more specific example, Styrolux (registered trademark) 684D which is styrene-butadiene block copolymer (SBC) available from BASF Corporation (USA), Cryro (registered trademark) R40 (acrylic base) which is acrylic-based multipolymer available from Cyro Industries (USA), Lexan KR01 which is polycarbonate available from SABIC Innovative Plastics (USA), K-resin (registered trademark) which is styrene-butadiene copolymer (SBC) available from Chevron Phillips Chemical Company (USA), TP-UXS (MMBS) (trade name) which is methyl methacrylate butadiene styrene terpolymer available from Denka Company Limited (Japan), Starex (registered trademark) 5010 which is acrylonitrile-butadiene-styrene resin (ABS) available from Samsung Cheil Industries (Korea), Zylar (registered trademark) 220 and Nas (registered trademark) 30 which are styrene-methyl methacrylic acid (SMMS) available from NOVA Chemicals (Canada), and Toyalac 920 (transparent ABS) which is acrylonitrile-butadiene-styrene (ABS) available from Toray Resin Company (USA) can be listed. As an example of mixing two or more kinds of resins, a mixture of ABS resin and polycarbonate can be listed. A metal available in the present invention is not particularly limited as long as it is not harmful to a living body, As an example, aluminum, silver, copper, gold, platinum, palladium, indium, iridium, iron, tin, cobalt, chromium, nickel, titanium, and alloy of the above metals can be listed, for example. As an example of the alloy, silver alloy, gold-silver-palladium alloy, gold alloy, alloy for baking ceramic, cobalt-chromium alloy, nickel-chromium alloy, and titanium alloy can be listed, for example. From a viewpoint of easiness in manufacturing, the band-shaped central region 3 and the insertion edge region 4, especially the screw impeller-shaped portion 4b, can be formed by a single material. Optionally, the band-shaped central region 3 and the insertion edge region 4 can be formed by a different material.

In the present invention, the hook portion 4a is formed on the downstream side in comparison to the screw impeller-shaped portion 4b of the insertion edge region 4 to hold the lateral nail edge of the nail or the lateral edge of the nail tip, and the hook portion is curved downward at an angle of 90° or more.

The definition of the angle of the curvature of the hook portion 4a is explained above with reference to FIG. 3.

The angle of the curvature of the hook portion 4a is generally 360° or less, preferably 300° or less, more preferably 270° or less, more preferably 230° or less, and more preferably 210° or less. The angle of the curvature of the hook portion 4a can be different between the upstream side and the downstream side. For example, the angle of the curvature of the hook portion 4a can be stepwisely increased from the upstream side to the downstream side. Alternatively, the angle of the curvature can be smoothly changed from the screw impeller-shaped portion 4b to the hook portion 4a so that the screw impeller-shaped portion 4b and the hook portion 4a are smoothly continued. Since the most optimal angle of the curvature varies depending on the patient, the angle of the curvature can be arbitrarily adjusted in accordance with the individual case when actually performing the treatment. A slip preventing means can be provided at the lowermost part of the hook portion 4a to prevent slip between the hook portion 4a and the lower surface of the nail. As an example of the slip preventing means, a hook-shaped portion facing upward and formed at the edge of the lowermost part of the hook portion 4a, and a projection formed on the hook portion 4a at a portion facing to the lower surface of the nail can be listed.

Same as the above described screw impeller-shaped portion 4b, the length of the hook portion 4a can be increased from the upstream side to the downstream side. In such a case, generally, the angle of the curvature is also increased from the upstream side to the downstream side. A plurality of hook portions 4a can be formed. In such a case, the hook portion 4a formed at the upstream side can be longer than the hook portion 4a formed at the downstream side. The length of the hook portion 4a (distance from the border between the hook portion 4a and the band-shaped central region 3 to the tip of the hook portion 4a measured along the width direction of the nail) is normally 1 to 10 mm, preferably 1.5 to 7 mm, and more preferably 2 to 5 mm.

About the insertion edge region 4, the width of the hook portion 4a measured along the longitudinal direction of the nail is normally 0.2 to 25 mm, preferably 0.5 to 15 mm, and more preferably 1.0 to 10 mm. The width of the screw impeller-shaped portion 4b measured along the longitudinal direction of the nail is normally 0.5 to 25 mm, preferably 2.0 to 15 mm, and more preferably 3.0 to 8.0 mm. The width of whole the insertion edge region 4 is normally 0.8 to 45 mm, preferably 2.5 to 25 mm, and more preferably 4 to 14 mm.

About the insertion edge region 4, the thickness of the hook portion 4a and the screw impeller-shaped portion 4b can be arbitrarily selected from a range of normally 0.03 to 5 mm, preferably 0.1 to 5 mm, more preferably 0.2 to 2 mm, and more preferably 0.4 to 1.0 mm. The thickness of the hook portion 4a and the thickness of the screw impeller-shaped portion 4b can be same or different as long as the thickness is within the above described range.

The screw impeller-shaped portion 4b and the hook portion 4a can be continuously formed or separately formed.

From the viewpoint of easiness in manufacturing and for reducing a patient burden when attaching the corrector, it is preferred that the screw impeller-shaped portion 4b and the hook portion 4a are continuously formed. In the embodiments shown in FIGS. 4 to 9, the screw impeller-shaped portion 4b and the hook portion 4a are continuously formed.

In the present invention, an extension portion extended from at least one selected from a group consisting of an end portion of the upstream side of the corrector and an end portion of the downstream side of the corrector can be provided to support to fix the corrector on the nail. The shape and dimension of the extension portion are not particularly limited as long as the extension portion can support to fix the corrector on the nail stably. In the present invention, at least one handle is preferably formed on an upper surface of the band-shaped central region or on an upper surface of the downstream side of the insertion edge region. By using such a handle, the corrector of the present invention can be efficiently and effectively inserted between the lateral nail edge and the lateral nail fold and adhered to the nail. Thus, the correcting force is efficiently and effectively applied. The handle can be removed after all operations applied to the nail are finished. The shape and dimension of the handle is not particularly limited as long as the handle can achieve the above described purpose.

In one embodiment of the corrector of the present invention, two insertion edge regions are extended from both ends of the band-shaped central region, the band-shaped central region has a shape to function as a pull spring, the two insertion edge regions are inserted into both left and right sides of the nail, and a force is applied to the nail to fasten the nail from the left and right sides of the nail when the corrector is attached to the nail. The specific shape of the band-shaped central region of the present embodiment is not particularly limited as long as the band-shaped central region functions as the pull spring to pull the two insertion edge regions toward the center. For example, the band-shaped central region can be formed into a flat spring having a bellows shape, W-shape, V-shape, or Ω-shape.

A manufacturing method of the corrector of the present invention is not particularly limited. Conventionally known manufacturing methods can be used. For example, when manufacturing the corrector of the present invention by using resin, the corrector can be directly manufactured by using conventionally known injection molding. Alternatively, the corrector can be manufactured by processing (e.g. cutting or bending) a flat plate made of resin. When manufacturing the corrector of the present invention by using metal, conventionally known methods such as die casting method, pressing method, sand casting method, forging method, machining method, and powder metallurgy method can be used, for example. The insertion edge region and the band-shaped central region can be integrally formed or separately formed and then attached to each other. When the insertion edge region and the band-shaped central region are separately formed and then attached to each other, a method of attaching is not particularly limited as long as the purpose of the present invention is achieved. For example, adhesion, welding and simple engagement can be listed.

Next, a method for correcting the deformed nail using the corrector of the present invention will be explained. First, the screw impeller-shaped portion 4b of the insertion edge region 4 of the corrector of the present invention is inserted between the lateral nail edge and the lateral nail fold. Then, the corrector is pushed into a direction of the root of the nail so that the hook portion 4a located at the downstream side of the screw impeller-shaped portion 4b holds the lateral edge of the nail tip or the lateral nail edge of the nail. When the corrector is pushed from the tip of the nail, the screw impeller-shaped portion 4b is initially entered between the lateral edge of the nail and the soft tissue smoothly as if the screw impeller-shaped portion 4b slides into there, and then the hook portion 4a is smoothly inserted into the root of the nail while being led by the screw impeller-shaped portion 4b. Since the hook portion 4a is smoothly led by the screw impeller-shaped portion 4b, the corrector of the present invention can be attached without imparting burdens to the soft tissue into which the nail is growing. When attaching the corrector of the present invention, the corrector can be pushed into the direction of the root of the nail while being rotated little by little to right and left when viewed from the front of the finger. After the corrector is positioned at a desired place on the nail, an adhesive agent is poured into between the insertion edge region 4 and the nail. After that, the band-shaped central region 3 is pulled so that the insertion edge region 4 is pulled toward the center of the nail. Thus, the curvature of the nail is corrected and the band-shaped central region 3 is adhered to the surface of the nail in a corrected state. (In the above described embodiment that two insertion edge regions 4 are extended from both ends of the band-shaped central region 3, the band-shaped central region 3 has a shape to function as a pull spring, the two insertion edge regions 4 are inserted into both left and right sides of the nail, and a force is applied to the nail to fasten the nail from the left and right sides of the nail when the corrector is attached to the nail, the attachment is completed when the corrector is positioned at a desired position on the nail (the adhesive agent is not required).) During the above described operation and before or after that, the correction of the lateral edge of the ingrown nail can be assisted by using tweezers or the ingrown nail corrector described in Patent Document 7. When several days or several weeks passed after the deformed nail is corrected to a normal shape using the corrector of the present invention by applying the above described operation, the corrector of the present invention is removed by using organic solvent such as a so-called "enamel remover" made mainly of acetone. The corrector can be removed by using a tool such as a knife and a nail file without using the organic solvent. If the corrector of the present invention is unintentionally removed from the nail before the correction is completed, the corrector is attached by applying the above described operation again.

Conventionally known adhesive agents can be used as an adhesive agent when adhering the band-shaped central region 3 on the surface of the nail and when the insertion edge region 4 and the nail are adhered with each other. As an example of the conventionally known adhesive agent, "Aron Alpha" (registered trademark) manufactured by Toagosei Co., Ltd. (Japan) can be listed. As an example of particularly preferred adhesive agent, Aron Alpha A "Sankyo" (registered trademark) which is an adhesive agent for medical use and manufactured by Toagosei Co., Ltd. (Japan) can be listed. Alternatively, an adhesive agent so-called "nail glue" which is generally used for attaching an artificial nail to one's own nail can be used, for example. Together with the nail glue, an activator (hardening accelerator) can be used for shortening the time required for adhesion. As a specific example of the nail glue, "ibd 5 Second Nail Glue" manufactured by shinwa Corporation (Japan) can be listed. As a specific example of the activator, "MITHOS Activator" manufactured by shinwa Corporation (Japan) can be listed.

The corrector of the present invention can be attached to the nail after the nail is softened and shaped by a nail softener including a substance acting as a reducing agent of disulfide bond. Namely, in another embodiment of the present invention, the corrector characterized to be used for the nail softened and shaped by a nail softener including a substance acting as a reducing agent of disulfide bond is provided. The nail can be softened by cutting the disulfide bond of cystine by the reducing agent. The cystine is an amino acid forming keratin protein, which is a main component of the nail. When using the nail softener, it is preferred that the shape of the nail is formed by using tweezers or the ingrown nail corrector described in Patent Document 7, an oxidizing agent is applied to the nail to cause disulfide bond again to restore the hardness of the nail to a certain extent in a state of being corrected, and then the corrector of the present invention is attached. After several days or several weeks have passed, the corrector of the present invention is removed. Thus, the correction of the deformed nail is completed.

As the nail softener (reducing agent of disulfide bond), a medical liquid generally sold as a so-called "permanent liquid" to be used for permanent wave can be used. Namely, the first agent of the commercially available permanent liquid can be used as the nail softener (reducing agent), while the second agent can be used as the oxidizing agent. As the reducing agent, thioglycolic acid, and salt or ester thereof can be used in general. As a more specific example, butyrolactonethiol, such as "Spiera" (registered trademark) manufactured by Showa Denko K.K. (Japan) and glyceryl monothioglycolate (GMT) can be listed. As an example of the oxidizing agent, hydrogen peroxide and bromate salt, such as potassium bromate and sodium bromate, can be listed.

An amount of the nail softener (reducing agent of disulfide bond) and the oxidizing agent applied can be decided so as to be uniformly applied to the surface of the nail. An appropriate amount of applying the nail softener or the oxidizing agent is normally within the range of 1 to 5 g, although the appropriate amount varies depending on the kind of the nail softener and the oxidizing agent and the size of the nail. The method of applying the nail softener and the oxidizing agent is not particularly limited. The method, such as a method using a brush, can be arbitrarily selected.

The inventor found that a free-end area (peripheral part of the nail separate from the nail bed) is enlarged by using the above described nail softener, and therefore the corrector of the present invention can be easily inserted into the root of the nail without giving pain to the patient in such situation. Thus, the effect of the present invention can be surely obtained because the curvature of the root of the nail is surely corrected.

For the serious ingrown nail, if the corrector of the present invention is used after the ingrown nail is softened by the nail softener and corrected by the corrector described in Patent Document 7, the correction can be more efficiently performed. The device described in Patent Document 7 is a devise for correcting the ingrown nail by lifting up a nail edge portion ingrown in the nail groove including: a vertical push-down member provided with a push-down head at a lower end of the push-down member; a lift-up angle maintaining means extended in a horizontal direction, the push-down member is attached to an intermediate part of the lift-up angle maintaining means; and a pair of lift-up members extended below from two positions of the lift-up angle maintaining means, the two positions are opposite to each other with respect to the intermediate part to which the push-down member attached, anchors are held on the lower end of the lift-up members, wherein the anchors have an adhesion surface at the lower surface of the anchors, the adhesion surface is adhered to the outer surface of the nail, the lift-up members are extended below from the lift-up angle maintaining means in the direction inclined from the central axis of the longitudinal direction of the nail when the adhesive surface of the anchors is adhered to the outer surface of the nail, the inclination between the lift-up members and the lift-up angle maintaining means at a joining part is 10° or more with respect to the vertical direction which is defined as the thickness direction of the finger having the nail, the push-down member is in contact with the intermediate portion of the outer surface of the nail when using the corrector, and the corrector is attached to the outer surface of the nail by adhering the adhesive surface of the pair of anchors to the lateral portions of the outer surface of the nail positioned opposite to each other with respect to the intermediate part with which the push-down head is contacted when viewed from the tip of the finger having the nail. Thus, a tension is applied to the lift-up members of the device attached to the nail, the lift-up force to correct the ingrown nail is applied to the anchors attached to both lateral portions of the external surface of the nail, and the intermediate portion of the external part of the nail is pushed toward the thickness direction of the finger by the push-down head of the push-down member.

As apparent from the above, the correction of the deformed nail using the corrector of the present invention can be performed by a method including the processes (1) to (5) below:

(1) a process of softening the nail by applying the nail softener, (2) a process of forming the shape of the nail (e.g. the shape of the nail can be formed by using the tweezers or the ingrown nail corrector described in Patent Document 7), (3) a process of applying an oxidizing agent on the nail, (4) a process of attaching and adhering the corrector of the present invention to the nail to fix the shape of the nail, and (5) a process of removing the corrector of the present invention from the nail after several days or several weeks have passed by dissolving the adhesive agent using organic solvent (e.g. enamel remover) or physically peeling off the corrector using a knife or a nail file.

When both lateral edges of the nail are ingrown, two correctors can be attached to the both lateral edges of the nail.

When attaching two correctors, one of the correctors is firstly attached to one of the lateral edges of the nail by using the above described method, and then the other of the correctors is attached to the other of the lateral edges by using the above described method. In this case, the band-shaped central regions of the both correctors are preferred to be laminated with each other and fixed by the adhesive agent. The conventionally known adhesive agents can be used as the above described adhesive agent. For example, the above described nail glue can be used. In some cases, the above described activator (hardening accelerator) can be simultaneously used. The correction can be more efficiently achieved by fixing the two correctors with each other as explained above. Furthermore, three or more correctors of the present invention can be attached to one nail if needed.

Another embodiment of the present invention provides a kit for correcting a deformed nail including a pair of deformed nail correctors formed in a band shape and configured to be attached to both left and right sides of a nail, each of the deformed nail corrector comprising:

a band-shaped central region configured to be in contact with an upper surface of the nail; and an insertion edge region continuously extended from at least one end of the band-shaped central region and configured to be inserted between a lateral nail edge and a lateral nail fold, wherein when a direction of a base side of the nail is defined as an upstream and a direction of a tip side of the nail is defined as a downstream in a state that the corrector is attached to the nail, a screw impeller-shaped portion is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip, the screw impeller-shaped portion has a shape curved downward at an angle of 90° or less, in a state that the deformed nail corrector is attached to the nail, a length of the screw impeller-shaped portion measured along the direction crossing the longitudinal direction of the nail is increased from the upstream side to the downstream side and is equal to or more than 5% of a width of the insertion edge region measured along the longitudinal direction of the nail, and the hook portion is curved downward at an angle of 90° or more.

The configuration, feature, material and manufacturing method of the pair of the correctors included in the kit for correcting a deformed nail of the present invention are same as those of the corrector of the present invention described above. The method of attaching each of the corrector to the nail is also same as described above.

Another embodiment of the present invention provides a system for correcting a deformed nail combining a pair of deformed nail correctors formed in a band shape and configured to be attached to both left and right sides of a nail, each of the deformed nail corrector comprising:

a band-shaped central region configured to be in contact with an upper surface of the nail; and an insertion edge region continuously extended from at least one end of the band-shaped central region and configured to be inserted between a lateral nail edge and a lateral nail fold, wherein when a direction of a base side of the nail is defined as an upstream and a direction of a tip side of the nail is defined as a downstream in a state that the corrector is attached to the nail, a screw impeller-shaped portion is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip, the screw impeller-shaped portion has a shape curved downward at an angle of 90° or less, in a state that the deformed nail corrector is attached to the nail, a length of the screw impeller-shaped portion measured along the direction crossing the longitudinal direction of the nail is increased from the upstream side to the downstream side and is equal to or more than 5% of a width of the insertion edge region measured along the longitudinal direction of the nail, the hook portion is curved downward at an angle of 90° or more, and the pair of the deformed nail correctors formed in the band shape are laminated at the band-shaped central region and fixed with each other by an adhesive agent.

The configuration, feature, material and manufacturing method of the pair of the correctors included in the system for correcting a deformed nail of the present invention are same as those of the corrector of the present invention described above. The conventionally known adhesive agent can be used to fix the pair of correctors formed in a band shape. For example, the above described nail glue can be used. In some cases, the above described activator (hardening accelerator) can be simultaneously used. Namely, the system for correcting a deformed nail can be formed by combining the kit for correcting a deformed nail on the nail using the above described method. The method of attaching each of the corrector to the nail is also same as described above.

Hereafter, the present invention will be explained by using examples. However, the present invention is not limited to the examples.

Example 1

Figure 4:
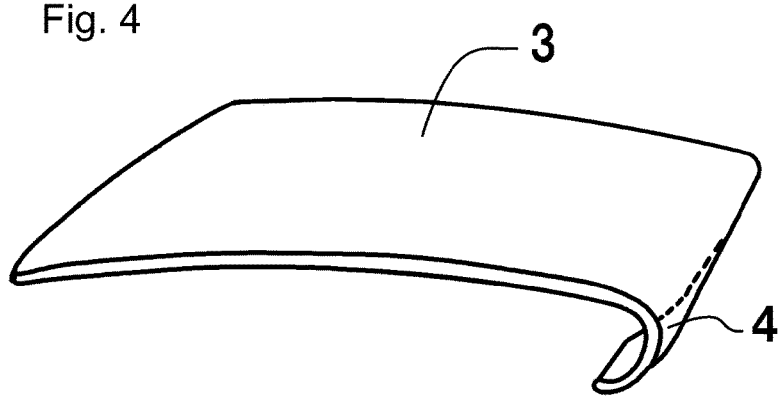
FIG. 4 is a schematic cross-sectional view of a corrector of one embodiment of the present invention seen obliquely from above.
Figure 5:
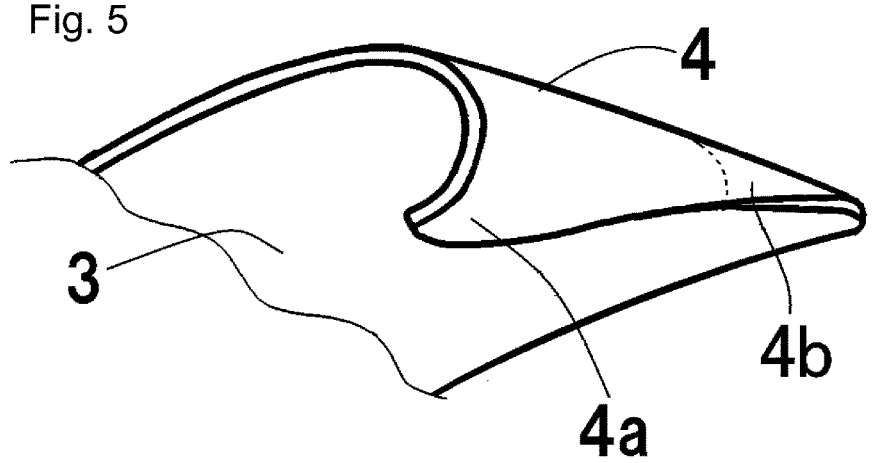
FIG. 5 is a schematic cross-sectional view of the corrector shown in FIG. 4 seen obliquely from below.
Figure 6:
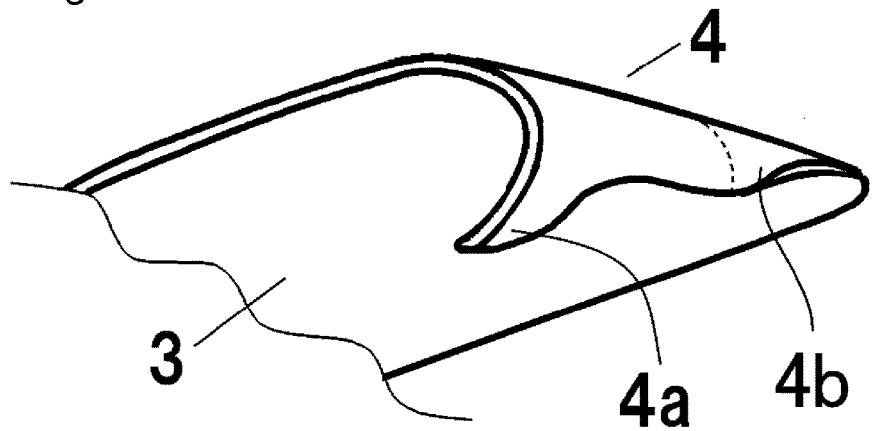
FIG. 6 is a schematic cross-sectional view of a corrector of another embodiment of the present invention seen obliquely from below.
Figure 7:
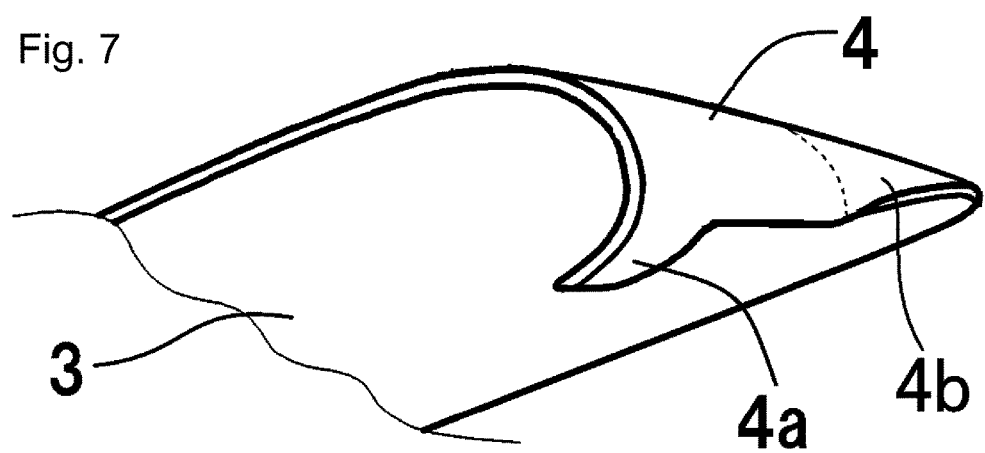
FIG. 7 is a schematic cross-sectional view of a corrector of another embodiment of the present invention seen obliquely from below.

The treatment for correcting the ingrown nail was applied to a female patient of 79-year-old by using the corrector made of polycarbonate and having a shape shown in FIG. 4.

1. Dimension of the Corrector

A length of the band-shaped central region 3 measured along the direction crossing the longitudinal direction of the nail: 15 mm A width of the band-shaped central region 3 measured along the longitudinal direction of the nail: 5 mm A thickness of the band-shaped central region 3: 0.5 mm A length of the hook portion 4a (distance measured along the width direction of the nail from the border between the hook portion 4a and the band-shaped central region 3 to the tip of the hook portion 4a): 2 mm A width of the hook portion 4a measured along the longitudinal direction of the nail: 3 mm A width of the screw impeller-shaped portion 4b measured along the longitudinal direction of the nail: 2 mm A rate of the width of the screw impeller-shaped portion 4b measured along the longitudinal direction of the nail with respect to the width of the insertion edge region 4: 40%

2. Method of Treatment

The nail was softened by applying 2 g of the nail softener (glyceryl monothioglycolate) to the nail of the patient, and then the shape of the softened nail was formed by using the tweezers. Then, 2 g of the oxidizing agent (potassium bromate) was applied to the nail. The above described corrector was inserted from the tip of the nail. Specifically, the insertion edge region 4 of the corrector was inserted between the lateral nail edge and the lateral nail fold of one side of the nail. At that time, although the corrector was pushed in until whole the corrector reaches the root side compared to the free edge of the tip of the nail, the corrector could be smoothly inserted without giving pain to the patient.

Then, the adhesive agent (Aron Alpha A "Sankyo" (registered trademark) manufactured by Toagosei Co., Ltd. (Japan)) was poured into between the insertion edge region 4 and the nail, and immediately after that, the band-shaped central region 3 of the corrector was adhered to the upper surface of the nail by using "IBD-5 Second Nail Glue" manufactured by shinwa Corporation (Japan)" and "MITHOS Activator" manufactured by shinwa Corporation (Japan). Thus, the corrector was adhered to the nail and fixed.

The correction treatment was also performed on the other side of the nail by applying the above described operation again.

After three weeks had passed, the adhesive agent was dissolved by using the enamel remover and the corrector of the present invention was removed from the nail.

3. Result

Figure 10A:
FIGS. 10A and 10B are photographs of a toe of a patient of the first example before and after the correction treatment.
Figure 10B:
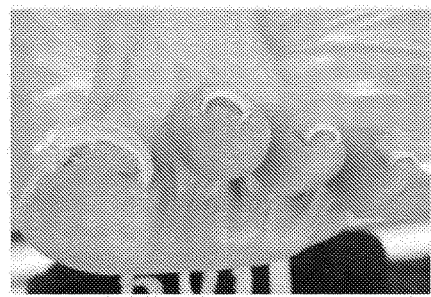

FIG. 10A shows a state of the ingrown nail before the correction treatment, and FIG. 10B shows a state after the correction treatment. Although less than 30 minutes were required for the above described correction treatment, as apparently shown in FIGS. 10A and 10B, serious ingrown nail was efficiently corrected in a short time. In FIG. 10B, it can be seen from the scar that the nail was primarily ingrown in the finger. In addition, the patient didn't feel uncomfortable and pain during the correction treatment. As explained above, the corrector was removed when three weeks passed after the treatment. However, the effect of the correction was maintained.

Example 2

The treatment same as the example 1 was applied to a male patient of 72-year-old.

FIG. 11A shows a state of the ingrown nail before the correction treatment, and FIG. 11B shows a state after the correction treatment. Also in this example, same as the example 1, serious ingrown nail was efficiently corrected in a short time. Same as the example 1, the patient didn't feel uncomfortable and pain during the correction treatment.

Comparative Example 1

The treatment for correcting the ingrown nail was performed by using the corrector having the same shape and size as the example used in Patent Document 5. The patient was a female of 55-year-old. The extent of the ingrown nail was almost same as the example 2.

Although the treatment was tried by using the same condition and operation as the example 1, about the attachment of the corrector to the nail, the patient complained about a pain when the corrector is tried to be pushed in the root of the nail. Therefore, the operation was performed in a state that the tip groove of the corrector was substantially inserted in only the free end located at the tip of the nail.

As a result, although the tip of the nail was corrected, the curvature of the root of the nail was not corrected. Thus, the patient had a recurrence of the ingrown nail when three month passed after the correction treatment.

INDUSTRIAL APPLICABILITY

Since the screw impeller-shaped portion and the hook portion are cooperated with each other, the corrector can be inserted into the lateral portion of the root of the nail without giving pain even for a serious ingrown nail which is significantly deformed and curved. In order to efficiently correct the nail, the lateral portion of the root of the nail is the most important portion. Thus, a great effect of the correction can be obtained while a patient burden is reduced. In addition, the deformation of the nail is prevented from occurring again.

DESCRIPTION OF REFERENCE SIGNS a: lower surface of nail
b: lateral surface of nail
c: upper surface of nail
d: center of circle indicated by broken line
e: starting point of curvature of insertion edge region f: tip portion of insertion edge region
α: angle of curvature
1: nail
2: big toe
3: band-shaped central region
4: insertion edge region
4a: hook portion
4b: screw impeller-shaped portion

What is claimed is:

1. A deformed nail corrector formed in a band shape and configured to be attached to a nail along a width direction of the nail, comprising:
   a band-shaped central region configured to be in contact with an upper surface of the nail; and
   an insertion edge region continuously extended from at least one end of the band-shaped central region and configured to be inserted between a lateral nail edge and a lateral nail fold, the insertion edge region configured for being inserted into the nail along a lateral edge of the nail, wherein
   when a direction of a base side of the nail is defined as an upstream and a direction of a tip side of the nail is defined as a downstream in a state that the corrector is attached to the nail, a screw impeller-shaped portion is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip,
   the screw impeller-shaped portion has a shape curved downward at an angle of 90° or less,
   in a state that the deformed nail corrector is attached to the nail, a length of the screw impeller-shaped portion measured along the width direction of the nail is increased from the upstream side to the downstream side and is equal to or more than 5% of a width of the insertion edge region measured along the longitudinal direction of the nail, and
   the hook portion is curved downward at an angle of 90° or more.

2. The deformed nail corrector according to claim 1, wherein
   when a maximum value of the length of the screw impeller-shaped portion is defined as 100%, a minimum value of the length of the screw impeller-shaped portion is 90% or less.

3. The deformed nail corrector according to claim 1, wherein
   when a maximum value of the length of the screw impeller-shaped portion is defined as 100%, a minimum value of the length of the screw impeller-shaped portion is 80% or less.

4. The deformed nail corrector according to claim 1, wherein
   the screw impeller-shaped portion includes at least one area selected from a group consisting of a first area where the length of the screw impeller-shaped portion is linearly increased from the upstream side to the downstream side, a second area where the length of the screw impeller-shaped portion is stepwisely increased from the upstream side to the downstream side, a third area where the length of the screw impeller-shaped portion is increased from the upstream side to the downstream side in a curvature swelling outward, and a fourth area where the length of the screw impeller-shaped portion is increased from the upstream side to the downstream side in a curvature recessed inward.

5. The deformed nail corrector according to claim 1, wherein
   at least the insertion edge region is formed of a flexible material.

6. The deformed nail corrector according to claim 1, wherein
   a length of the band-shaped central region measured along the width direction of the nail is more than 50% of a width of the nail to which the deformed nail corrector is attached.

7. The deformed nail corrector according to claim 1, further comprising:
   an extension portion that is extended from at least one selected from a group consisting of the end portion of the upstream side of the deformed nail corrector and an end portion of the downstream side of the deformed nail corrector to support and to fix the deformed nail corrector on the nail.

8. The deformed nail corrector according to claim 1, wherein:
   at least one handle is formed on an upper surface of the band-shaped central region.

9. The deformed nail corrector according to claim 1, wherein:
   two insertion edge regions are extended from both ends of the band-shaped central region, the band-shaped central region has a shape to function as a pull spring, the two insertion edge regions are configured to be inserted into both left and right sides of the nail, and a force is applied to the nail to fasten the nail from the left and right sides of the nail when the deformed nail corrector is attached to the nail.

10. The deformed nail corrector according to claim 1, wherein:
    the deformed nail corrector is used for the nail softened and shaped by a nail softener including a substance acting as a reducing agent of disulfide bond.

11. A kit for correcting a deformed nail including a pair of deformed nail correctors formed in a band shape and configured to be attached to both left and right sides of a nail, each of the deformed nail correctors comprising:
    a band-shaped central region configured to be in contact with an upper surface of the nail; and
    an insertion edge region continuously extended from at least one end of the band-shaped central region and configured to be inserted between a lateral nail edge and a lateral nail fold, the insertion edge region configured for being inserted into the nail along a lateral edge of the nail, wherein
    when a direction of a base side of the nail is defined as an upstream and a direction of a tip side of the nail is defined as a downstream in a state that the corrector is attached to the nail, a screw impeller-shaped portion is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip,
    the screw impeller-shaped portion has a shape curved downward at an angle of 90° or less,
    in a state that the deformed nail corrector is attached to the nail, a length of the screw impeller-shaped portion measured along a width direction of the nail is increased from the upstream side to the downstream side and is equal to or more than 5% of a width of the insertion edge region measured along the longitudinal direction of the nail, and the hook portion is curved downward at an angle of 90° or more.

12. A system for correcting a deformed nail combining a pair of deformed nail correctors formed in a band shape and configured to be attached to both left and right sides of a nail, each of the deformed nail corrector comprising:

a band-shaped central region configured to be in contact with an upper surface of the nail; and an insertion edge region continuously extended from at least one end of the band-shaped central region configured to be inserted between a lateral nail edge and a lateral nail fold, the insertion edge region configured for being inserted into the nail along a lateral edge of the nail, wherein when a direction of a base side of the nail is defined as an upstream and a direction of a tip side of the nail is defined as a downstream in a state that the corrector is attached to the nail, a screw impeller-shaped portion is formed on a portion including an end portion of an upstream side of the insertion edge region and a hook portion is formed on a downstream side of the insertion edge region in comparison to the screw impeller-shaped portion to hold the lateral nail edge of the nail or a lateral edge of a nail tip, the screw impeller-shaped portion has a shape curved downward at an angle of 90° or less, in a state that the deformed nail corrector is attached to the nail, a length of the screw impeller-shaped portion measured along a width direction of the nail is increased from the upstream side to the downstream side and is equal to or more than 5% of a width of the insertion edge region measured along the longitudinal direction of the nail, the hook portion is curved downward at an angle of 90° or more, and the pair of the deformed nail correctors formed in the band shape are laminated at the band-shaped central region and fixed with each other by an adhesive agent.

13. The deformed nail corrector according to claim 1, wherein:

a curvature angle of the screw impeller-shaped portion is gradually increased from the upstream side to the downstream side.

14. The deformed nail corrector according to claim 1, wherein:

a curvature angle of the screw impeller-shaped portion is different between the upstream side and the downstream side.

* * * * *